Figure 1:
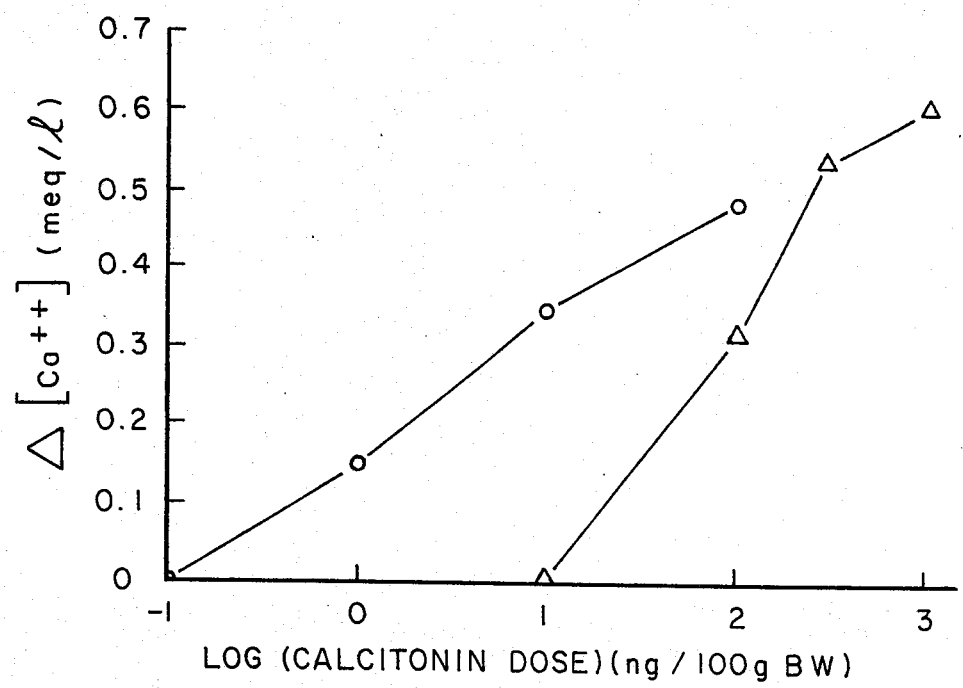

United States Patent [19]

Kaiser et al.

[11] Patent Number: 4,663,309
[45] Date of Patent: * May 5, 1987

[54] NOVEL PEPTIDE HORMONES WITH CALCITONIN-LIKE ACTIVITY

[75] Inventors: Emil T. Kaiser; Gregory R. Moe, both of New York, N.Y.

[73] Assignee: University Patents, Inc., Westport, Conn.

[*] Notice: The portion of the term of this patent subsequent to Apr. 30, 2002 has been disclaimed.

[21] Appl. No.: 713,726
[22] PCT Filed: Jun. 28, 1984
[86] PCT No.: PCT/US84/01026
 § 371 Date: Feb. 27, 1985
 § 102(e) Date: Feb. 27, 1985
[87] PCT Pub. No.: WO85/00165
 PCT Pub. Date: Jan. 17, 1985

Related U.S. Application Data

[63] Continuation-in-part of Ser. No. 509,123, Jun. 29, 1983, Pat. No. 4,514,331.

[51] Int. Cl.⁴ .................. A61K 37/24; C07K 7/36
[52] U.S. Cl. .................................. 514/11; 514/808; 530/307
[58] Field of Search .................. 260/112.5 T; 514/11, 514/808; 530/307

[56] References Cited

U.S. PATENT DOCUMENTS

| | | | |
|---|---|---|---|
| 3,798,203 | 3/1974 | Brugger et al. | 260/112.5 |
| 3,849,388 | 11/1974 | Rittel et al. | 260/112.5 |
| 3,926,938 | 12/1975 | Hughes et al. | 260/112.5 |
| 3,988,309 | 10/1976 | Matsuda et al. | 260/112.5 T |
| 4,033,940 | 7/1977 | Hughes et al. | 260/112.5 R |
| 4,062,815 | 12/1977 | Hughes et al. | 260/112.5 R |
| 4,086,221 | 4/1978 | Sakakibava et al. | 260/112.5 T |
| 4,086,334 | 4/1978 | Schmidt-Dunker et al. | 260/112.5 T |
| 4,159,981 | 7/1979 | Rittel et al. | 260/112.5 T |
| 4,391,747 | 7/1983 | Orlowski et al. | 260/112.5 T |
| 4,401,593 | 8/1983 | Orlowski et al. | 260/112.5 T |
| 4,514,331 | 4/1985 | Kaiser et al. | 260/112.5 T |

FOREIGN PATENT DOCUMENTS

| | | |
|---|---|---|
| 82303666.0 | 1/1983 | European Pat. Off. . |
| 83302916.8 | 11/1983 | European Pat. Off. . |
| US83/00562 | 11/1983 | PCT Int'l Appl. *. |
| GB83/00172 | 2/1984 | PCT Int'l Appl. . |
| 1314051 | 4/1973 | United Kingdom . |
| 1320298 | 6/1973 | United Kingdom . |
| 1590645 | 6/1981 | United Kingdom . |
| 2135320A | 8/1984 | United Kingdom . |

OTHER PUBLICATIONS

Adamson, A. W., *Physical Chemistry of Surfaces*, 3rd Ed. (Wiley, Interscience, New York, 1976), p. 388.

Ames, B. N. and D. T. Dubin, J. Biol. Chem., 235(3):769-775 (1960).

Barany, G. and R. B. Merrifield, In *The Peptides*, vol. 2, (E. Gross and J. Meienhofer, eds.) (Academic Press, New York, 1979), pp. 3-284.

Batzri, S. and E. D. Korn, Biochim. Biophys. Acta, 292:1015-1019 (1973).

Behrens & Grinnan, Ann. Rev. Biochem., 38-83 (1969).

Birnbaumer, L., P. C. Yang, M. Hunzicker-Dunn, J. Bockaert, and J. M. Duran, Endocrin., 99:163 (1976).

Brewer, H. B. and H. Edelhoch, J. Biol. Chem., 245(9): 2402-2408 (1970).

Chou, P. Y. and G. D. Fasman, Ann. Rev. Biochem., 47:251-276 (1978).

Edelstein, C., F. J. Kezdy, A. M. Scanu, and B. W. Shen, J. Lipid Res., 20:143-153 (1979).

Finn, F. M. and K. Hofmann, In *Proteins*, vol. 2, 3rd Ed. (H. Neurath and R. L. Hill, eds.) (Academic Press, New York, 1976), pp. 105-253.

Foster, G. V., P. G. H. Byfield and T. V. Gudmundsson, In *Clinics in Endocrinology and Metabolism*, pp. 93-124 (1972).

Greenfield, N. and G. D. Fasman, Biochem., 10:4108-4115 (1969).

Guttman, S. in *Calcitonin* 1980 (Pecile, A., ed.) (Excerpta Medica, Princeton, N.J., 1981), pp. 11-24.

Hruby, V. J., D. A. Upson, and N. S. Agarwal, J. Org. Chem., 42(22):3552-3556 (1977).

Hunter, W. M. and F. C. Greenwood, Nature, 194 (4827):495-496 (1962).

Kupferberg, J. P., S. Yokoyama, and F. J. Kezdy, J. Biol. Chem., 256(12): 6274-6281 (1981).

(List continued on next page.)

Lehninger, A. L., Biochemistry, 2nd Ed. (Worth Publishers, Inc., New York, 1975), pp. 73–75.
MacIntyre, I., I. M. A. Evans, H. H. G. Hobitz, G. F. Joplin, and J. C. Stevenson, Arthritis and Rheumatism, 23(10):1139–1147 (1980).
Maier, R., B. Kamber, B. Riniker and W. Rittel, Clin. Endocrin., 5, Suppl:3275–3325 (1976).
Marcus, R. and G. D. Aurbach, Biochim. Biophys. Acta, 242:410–421 (1971).
Marx, S. J., C. J. Woodard, and G. D. Aurbach, Science, 178:999–1000 (1972).
Moe, G. R. and E. T. Kaiser, Biochem., 24:1971–1976 (1985).
Morikawa, T., E. Munekata, S. Sakakibara, T. Noda and M. Otani, Experientia, 32(9):1104–1106 (1976).
Morrisett, J. D., J. S. K. David, H. J. Pownall, and A. M. Gotto, Jr., Biochem., 12(7):1290–1299 (1973).
Nakagawa, S. H. and E. T. Kaiser, J. Org. Chem., 48:678–685 (1983).
Nakamuta, H., S. Furukawa, M. Koida, H. Yajima, R. C. Orlowski and R. Schlueter, Japan J. Pharmacol., 31:53–60 (1981).
Noda, T. and K. Narita, J. Biochem., 79:353–359 (1976).
Pietta, P. G. and G. R. Marshall, Chem. Comm., 1970:650–651.
Pollett, R. J., B. A. Haase, and M. L. Standaert, J. Biol. Chem., 254(1):30–33 (1979).
Schwartz, K. E., R. C. Orlowski, and R. Marcus, Endocrin., 108(3):831–835 (1981).
Sedmak, J. J. and S. E. Grossberg, Anal. Biochem., 83:544 (1977).
Yamashiro, D. and C. H. Li, J. Am. Chem. Soc., 100(16):5174–5179 (1978).
Science News, 93:545–546 (6/8/68).

*Primary Examiner*—Delbert R. Phillips
*Attorney, Agent, or Firm*—Barbara A. Shimei

[57] ABSTRACT

Compounds of the formula:

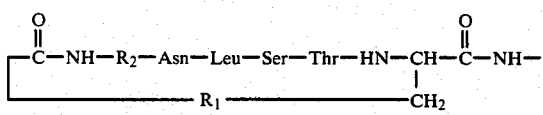

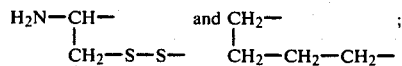

wherein
$R_1$ is a moiety selected from the group consisting of $$H_2N-CH- \quad \text{and} \quad CH_2- \atop CH_2-S-S- \quad CH_2-CH_2-CH_2-$$

$R_2$–$R_{22}$ are amino acid moieties wherein
  $R_2$ is an optional moiety which when present is selected from the group consisting of Ser and Gly,
  $R_8$ is Leu or Val,
  $R_{10}$ is Gln, Lys, or Gly,
  $R_{11}$, $R_{14}$, and $R_{20}$ are each independently selected from the group consisting of Gln and Lys,
  $R_{12}$ is Leu or Trp,
  $R_{13}$ is Gln or Ser,
  $R_{17}$ is Gln or His,
  $R_{19}$ is Leu or Cys,
  $R_{21}$ is Gln or Thr,
  $R_{22}$ is an optional moiety which when present is selected from the group consisting of Leu and Tyr;
$R_{24}$–$R_{31}$ comprise a series of eight amino acids each independently selected from the group consisting of Gly, Ser, Thr, Cys, Tyr, Asn, Gln, Asp, Glu, Lys, Arg, and His, with the proviso that not more than one of said eight amino acids may be selected from the group consisting of Asp, Glu, Lys, Arg, and His, and with the proviso that no four or more of said eight amino acids will spontaneously form helical, β-sheet, or β-turn conformations; with the further proviso that when $R_{19}$ is Cys, $R_{24}$ must also be Cys linked to $R_{19}$ via a disulfide bridge; and
$R_{32}$ is an amino acid amide selected from the group consisting of proline amide and glycine amide;

the pharmaceutically acceptable salts thereof, compositions containing said compounds, and methods of lowering serum calcium levels using said compounds.

25 Claims, 8 Drawing Figures

NOVEL PEPTIDE HORMONES WITH CALCITONIN-LIKE ACTIVITY

This application is a continuation-in-part of copending U.S. application Ser. No. 509,123, filed June 29, 1983 now U.S. Pat. No. 4,514,331 issued Apr. 30, 1985.

The invention described herein was made in the course of work under a grant from the National Institutes of Health.

This invention relates to novel peptide hormones which exhibit calcitonin-like activity, to the pharmaceutically acceptable non-toxic salts thereof, to compositions containing said hormones, and to methods of lowering serum calcium levels by the administration of said hormones.

Calcitonin is a peptide hormone with a molecular weight of approximately 3,500 daltons which is produced by the parafollicular cells; these cells are scattered throughout the thyroid in mammals but in lower animals constitute a distinct organ, the ultimobranchial body. The hormone regulates serum calcium concentrations by opposing the bone and renal effects of parathyroid hormone and inhibiting bone resorption of calcium, resulting in hypocalcemia, hypophosphatemia, and decreased urinary calcium concentrations. Calcitonin is therefore used in the treatment of Paget's Disease, hyperparathyroidism, idiopathic hypercalcemia of infancy, osteolytic bone metatases, and to counteract the osteolytic effect of overdoses of vitamins A and D.

Calcitonins from at least seven different species, and the two isohormones of salmon calcitonin, have been sequenced and characterized biologically and a number of synthetic analogs have been studied, but few clear correlations between structure and function have been made. The common form of the hormone consists of 32 amino acids with a disulfide bridge between cysteine residues at positions 1 and 7 and prolinamide at the carboxy terminus. All natural forms of calcitonin have a hydrophilic amino acid at position 15, usually aspartate or glutamate. The mammalian forms all have aromatic amino acids at positions 12, 16, and/or 19, while the ultimobranchial peptides do not. As a group, mammalian calcitonins are between 10 and 50 times less potent than those of ultimobranchial origin (Guttman, S. in *Calcitonin 1980: Chemistry, Physilogy, Pharmacology and Clinical Aspects* (Pecile, A., ed.) (Exerpta Medica, Princeton, N.J., 1981), p. 11). Otherwise the structures of the various calcitonins differ markedly from each other; human calcitonin differs from porcine calcitonin at 18 of the 32 residues. It is generally recognized that the cysteines at positions 1 and 7 taken together may be replaced by 2-aminooctanedioic acid, resulting in the analogous structure wherein the disulfide bridge of the cysteines has been replaced by an ethylene bridge. For a general review, see MacIntryre, I., I. M. A. Evans, H. H. G. Hobitz, G. F. Joplin, and J. C. Stevenson, Arth. Rheum. 23:1139–1147 (1980); Guttman, supra.

Because of its therapeutic value, calcitonin is in great demand. Of the known calcitonins and their analogs, only three, salmon, porcine, and human, are commercially available. Porcine calcitonin is isolated and purified at great expense from pork glands, whereas salmon and human calcitonin are primarily synthesized in vitro. Salmon calcitonin is the most active of the known calcitonins, and porcine is the most active commercially available mammalian calcitonin. However, because foreign calcitonins tend to trigger an antigenic response, and because human calcitonin is only weakly active, there is a need for improved synthetic alternate peptide hormones with calcitonin-like activity.

Maier, R., B. Kamber, B. Riniker, and W. Rittel, Clin. Endocrin. 5(Suppl.):327s–332s (1976) showed that sequentially substituting leucine for aromatic amino acids in positions 12, 16, and 19 of human calcitonin significantly increased its efficiency. However, they were unable to obtain an analog with activity equal in potency to salmon calcitonin. There is therefore a need to further understand the elements required for activity so that these compounds can be modified to introduce desired pharmaceutical characteristics, such as increased half-life or oral activity, without losing efficacy.

It has now been discovered that compounds of the Formula I:

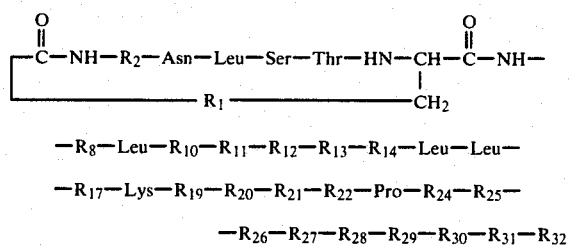

$$-R_8-Leu-R_{10}-R_{11}-R_{12}-R_{13}-R_{14}-Leu-Leu-$$
$$-R_{17}-Lys-R_{19}-R_{20}-R_{21}-R_{22}-Pro-R_{24}-R_{25}-$$
$$-R_{26}-R_{27}-R_{28}-R_{29}-R_{30}-R_{31}-R_{32}$$

wherein
$R_1$ is a moiety selected from the group consisting of

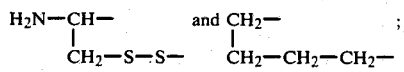

$R_2$-$R_{22}$ are amino acid moieties wherein
$R_2$ is an optional moiety which when present is selected from the group consisting of Ser and Gly (i.e., $R_2$ can be absent, but when present is Ser or Gly),
$R_8$ is Leu or Val,
$R_{10}$ is Gln, Lys, or Gly,
$R_{11}$, $R_{14}$, and $R_{20}$ are each independently selected from the group consisting of Gln and Lys,
$R_{12}$ is Leu or Trp,
$R_{13}$ is Gln or Ser,
$R_{17}$ is Gln or His,
$R_{19}$ is Leu or Cys,
$R_{21}$ is Gln or Thr,
$R_{22}$ is an optional moiety which when present is selected from the group consisting of Leu and Tyr (i.e., $R_{22}$ can be absent, but when present is Leu or Tyr);
$R_{24}$-$R_{31}$ comprise a series of eight amino acids each independently selected from the group consisting of Gly, Ser, Thr, Cys, Tyr, Asn, Gln, Asp, Glu, Lys, Arg, and His, with the proviso that not more than one of said eight amino acids may be selected from the group consisting of Asp, Glu, Lys, Arg, and His, and with the proviso that no four or more of said eight amino acids will spontaneously form helical, β-sheet, or β-turn configurations; with the further proviso that when $R_{19}$ is Cys, $R_{24}$ must also be Cys linked to $R_{19}$ via a disulfide bridge; and
$R_{32}$ is an amino acid amide selected from the group consisting of proline amide and glycine amide
have calcitonin-like activity in vivo. It has also been discovered that in addition to the 7-amino acid sequence at the amino end of the peptide with cysteine residues at positions 1 and 7 linked by a disulfide bridge (or with 2-aminooctanedioic acid replacing these two cysteines), which sequence can be designated as Section 1 of the peptide hormone, the following features are essential to activity:

Section 2: A 15-amino acid sequence at positions 8-22, which sequence spontaneously forms an amphiphilic helix characterized in that the hydrophilic amino acid residues are segregated along one side of the vertical axis of the helix while the hydrophobic amino acid residues are segregated along the opposite side of the vertical axis of the helix. Residues are considered hydrophobic if their hydrophobicity parameter as defined by Edelstein, C., F. J. Kezdy, A. M. Scanu, and B. L. Shen, J. Lipid Res. 20:148 1 (1979), is greater than or equal to 0.5 and hydrophilic if the parameter is less than 0.5. The average α-helicity parameter, $<P_\alpha>$, as described by Chou, P. Y. and G. D. Fasman, Ann. Rev. Biochem. 47:25-76 (1978) must be greater than 1.03, and no more than half of the hydrophilic amino acid residues may be charged at pH 6.0-7.0.

Section 3: A 10-amino acid sequence at positions 23-32 (carboxy-terminal end of the peptide) having a proline residue at position 23 and an amino acid amide residue at position 32. These 10 amino acid residues are hydrophilic and no more than one may be charged at pH 6.0-7.0. They are selected to form a "random chain" so that no four or more of said 10 amino acids will spontaneously assume a helical, β-sheet, or β-turn configuration according to the empirical predictive parameters defined by Chou and Fasman, supra.

These characteristics of the helix are more readily visualized when the compounds of the present invention are depicted in the following form:

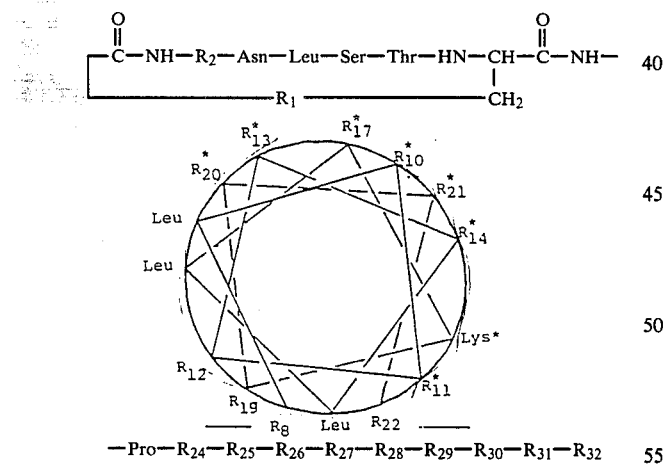

wherein $R_1$-$R_{32}$ are as previously defined. The hydrophilic amino acid residues in the helix are marked by an asterisk (*); the unmarked residues are hydrophobic. From this depiction it can be easily be seen that the hydrophobic and hydrophilic residues are segregated on opposite sides of the helix. It is believed that this configuration is necessary for the interaction of the hormone with its specific receptor sites.

As used hereinabove and below, the three-letter abbreviations for the amino acid residues are those commonly used and accepted by persons in the peptide art; see, e.g., Lehninger, Albert L., Biochemistry, 2nd Ed. (Worth Publishers, Inc., New York, 1975), pp. 73-75. All amino acids and their derivatives are in the L-form.

Preferably, $R_8$ is Leu; $R_{10}$ is Gln or Lys; and $R_{13}$, $R_{17}$, and $R_{21}$ are each Gln. Particularly preferred are compounds of the Formula II (which has been designated "MCT-I"):

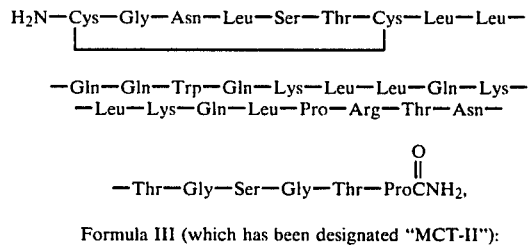

Formula III (which has been designated "MCT-II"):

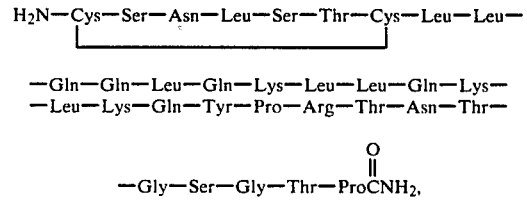

and Formula IV (which has been designated "MCT-III"):

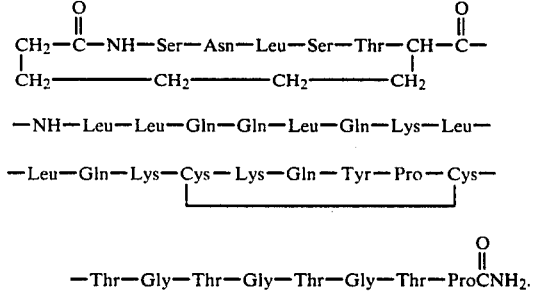

The basic amino acid residues (lysine, arginine, and histidine) of the compounds of Formula I may be in the form of their acid-addition salts. The hydrochloride, acetate, phosphate, citrate, fumarate, maleate, succinate, pamoate, and sulfate acid-addition salts are preferred. Particularly preferred are the acetate and hydrochloride salts. It is to be understood that for the purposes of this invention, the acid-addition salts of the hormones of Formula I are equivalent to the parent free peptide.

The compounds of Formula I may be synthesized by methods well-known to those skilled in the art of peptide synthesis, e.g. solution phase synthesis (see Finn, F. M. and K. Hofmann, in Proteins, Vol. 2, 3rd Ed. (H. Heurath and R. L. Hill, eds.) (Academic Press, New York, 1976), pp. 105-253), or solid phase synthesis (see Barany, G. and R. B. Merrifield, in The Peptides, Vol. 2 (E. Gross and J. Meienhofer, eds.) (Academic Press, New York, 1979) pp. 3-284). Preferably these compounds are synthesized by the solid phase method on a benzhydrylamine-substituted polystyrene resin cross-linked with 1% divinylbenzene, see Pietta, P. G. and G. R. Marshall, J. Chem. Soc. D: 650-651 (1970); Hruby, V. J., D. A. Upson, and N. S. Agarwal, J. Org. Chem. 43: 3552 (1977). The α-amino group of the carboxy-terminal amino acid ($AA_{32}$) is first shielded with a selectively cleavable N-terminal protecting group. Preferably, this group is t-butoxycarbonyl (Bα). Amino acids with the $N^\alpha$-Boc shielding group in place are commercially available from, e.g., Bachem Inc., Marina Del Rey, Calif., and Peninsula Laboratories, San Carlos, CA. The blocked amino acid ($N^\alpha$-Boc-$AA_{32}$) is then coupled to the resin using N-hydroxybenzotriazole (HOBt) in conjunction with dicyclohexylcarbodiimide (DCC) as condensing agents. The $N^\alpha$-Boc group is subsequently removed by treatment with a strong anhydrous organic acid, preferably trifluoroacetic acid neat or about 25–75% (50% preferred) in methylene chloride, at about 20°–30° C. for about 30–60 minutes. The reaction mixture is then neutralized with a hindered organic base, e.g. diisopropylethylamine or N-ethylmorpholine, preferably about 2–10% diisopropylethylamine in methylene chloride at about 20°–30° C. for about 2–6 minutes. The amino acid of position 31 ($AA_{31}$) is then added to the N-terminal amine of $AA_{32}$ by reaction with the symmetric anhydride or active ester of $N^\alpha$-Boc-$AA_{31}$ in the presence of methylene chloride at about 20°–30° C. for about 20–60 minutes, followed by removal of the $N^\alpha$-Boc blocking group of $AA_{31}$ by treatment with about 25–75% (50% preferred) trifluoroacetic acid in methylene chloride at about 20°–30° C. for about 30–60 minutes. In a similar manner, the remaining amino acid residues are added in sequence and the peptide chain is built up from the C-terminal end, except for $N^\alpha$-BocAsn, which is added by the HOBt/DCC method above. See Yamashiro, D. and C. H. Li, J. Am. Chem. Soc. 100:5174 (1978).

If $R_1$ is to be

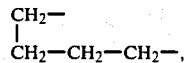

the C-2 amino group and the C-8 carboxyl group of 2-aminooctanedioic acid are first protected ($N^\alpha$-Boc, $O^\eta$-t-Bu, respectively) when the growing peptide chain has reached the point where $AA_8$ ($R_8$) is in position, the C-1 carboxy on the shielded 2-aminooctanedioic acid is bonded to the $\alpha$-amine moiety of $AA_8$. The $\alpha$-carboxyl group of $AA_6$ is then added to the C-2 amine of the 2-aminooctanedioic acid; after deprotection, $AA_5$ is added to $AA_6$, and so on through $AA_2$. The C-8 carboxyl group on the 2-aminooctanedioic acid is then activated (HOBt/DCC) to allow it to react with the $\alpha$-amino moiety of $AA_2$. Thus the two halves of 2-aminooctanedioic acid each function as a separate amino acid at positions 1 and 7, linked through an ethylene bridge. For details on methods of incorporating 2-aminooctanedioic acid in the proper positions, see Morikawa, T. et al., Experientia 32: 1104–1106 (1976).

It is understood by those skilled in the art that certain amino acids contain reactive side groups which must be shielded during the coupling reaction. Thus the N-guanidinium moiety of $N^\alpha$-BocArg is tosylated to yield $N^\alpha$-BocArg($N^g$-Tos). The thiol group of $N^\alpha$-BocCys is protected by a 4-methoxybenzyl moiety to yield $N^\alpha$-BocCys(S-4-MeOBzl). $N^\alpha$-BocLys is converted to $N^\alpha$-BocLys($N^\epsilon$-2-ClZ) wherein the $\alpha$-amino of lysine is protected by a 2-chlorobenzyloxycarbonyl moiety. $N^\alpha$-BocSer(OBzl) and $N^\alpha$-BocThr(OBzl) are formed from $N^\alpha$-BocSer and $N^\alpha$-BocThr, respectively; the hydroxy groups of serine and threonine are converted to an ether linkage with the benzyl moiety. In a similar manner, the hydroxy group of $N^\alpha$-BocTyr is converted to an ether linkage with a 2,6-dichlorobenzyl moiety to yield $N^\alpha$-BocTyr(O-2,6-$Cl_2$Bzl). The indole nitrogen of $N^\alpha$-BocTrp is formylated for protection to yield $N^\alpha$-BocTrp($N^{in}$-For). These shielded amino acids may be prepared according to methods given in Barany and Merrifield, supra, pp. 169–250, or they may be obtained commercially from, e.g., Bachem Inc. or Peninsula Laboratories.

The shielded amino acid residues are converted to their symmetrical anhydrides by reaction with DCC in methylene chloride in a ratio of 2 molar equivalents of amino acid per molar equivalent of DCC at about 5°–10° C. for about 15 minutes. The resulting product is suitable for use without further isolation and purification. Alternatively, the shielded amino acids are converted to their active esters by reaction with HOBt and DCC in a ratio of 1:1:1 molar equivalents.

The completed peptide is cleaved from the resin with simultaneous removal of all protecting groups except the $N^{in}$-formyl by treatment with anhydrous liquid hydrofluoric acid:anisole (7–9:1, v/v) at 0° C. for about 30–60 min. One of the advantages of the benzhydrylamine-substituted polystyrene resin used is that the carboxy-terminal amino acid residue ($AA_{32}$) is spontaneously yielded in its amino acid amide form upon cleavage. Crude peptide is removed from the resin by washing with 5–20% acetic acid. Ten percent acetic acid is preferred.

The crude peptide is then preferably lyophilized. During cleavage from the resin, any cysteine residues present may have oxidized. The thiol groups are reduced to their free form by treatment with a reducing agent such as excess dithiothreitol or $\beta$-mercaptoethanol in a mild physiological buffer such as sodium phosphate or carbonate, tris, MOPS, etc. Sodium phosphate (0.05M, pH 7.0) is preferred.

If $R_1$ is to be

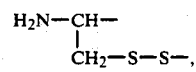

the peptide solution solution is diluted in the same buffer as above to a volume of about 5 liters and a solution of 0.02M $K_3Fe(CN)_6$ (oxidizing agent) is added slowly with stirring at 20°–30° C. to induce the formation of the disulfide bridge between the cysteine residues at positions 1 and 7. Oxidation may also be accomplished by air oxidation (e.g., by bubbling air or oxygen through the dilute peptide solution).

The peptide is then concentrated and purified by procedures well-known to those skilled in the art, e.g. by molecular sieving, ion exchange chromatography, HPLC, evaporation, lyophilization, etc., and the $N^{in}$-formyl group is removed. Preferably, the peptide is concentrated and purified by absorption on an ion exchange column such as CM-Sephadex C-25 ™ (Pharmacia Fine Chemicals, Piscataway, N.J.), followed the elution with a linear salt gradient, e.g. 0.0 to 0.3M NaCl in the same buffer used to form the bridge moiety. The peptide elutes in about 2.8M NaCl and is further purified by HPLC using a linear gradient of from about 20–50% acetonitrile in 0.2M sodium phosphate buffer, pH 2.5. The resulting solution is desalted and the $N^{in}$-formyl protecting group is removed quantitatively by treatment with a nucleophilic species in aqueous solution, e.g. by piperidine, sodium hydroxide or hydrazine, preferably 0.5M aqueous piperidine, at 0° C. for about 20 minutes. The deprotective reaction is terminated by addition of acid, preferably acetic acid. Alternatively, the N$^{in}$-formyl group may be removed by methods given in Barany and Merrifield, supra, p. 220. The peptide is then once again purified by HPLC, eluting with about 35% acetonitrile in 0.2M sodium phosphate buffer, pH 2.5.

The acid-addition salts of the basic amino acid residues are prepared by treatment of the peptide with the appropriate organic or inorganic acid according to procedures well-known to those skilled in the art; or the desired salt may be obtained directly by lyophilization out of the appropriate acid.

The compounds of formula I are useful to lower the serum plasma calcium level in warm-blooded animals suffering from elevated serum plasma calcium levels when administered in amounts ranging from about 0.1 ng to about 10 ng per kg of body weight per day. A preferred dosage range for optimal results would be from about 0.15 ng to about 8 ng per kg of body weight per day, and such dosage units are employed so that a total of from about 0.1 mg to about 0.56 mg of the active compound for a subject of about 70 kg of body weight are administered in a 24-hour period. This dosage regimen may be adapted to provide the optimum therapeutic response. For example, several divided doses may be administered daily, or the dose may be proportionally reduced as indicated by the exigencies of the therapeutic situation. The compound may be administered in the form of the free peptide or as a non-toxic pharmaceutically acceptable salt thereof. The term "pharmaceutically acceptable salt" refers to those acid-addition salts of the parent compound which do not significantly adversely affect the pharmaceutical properties (e.g. toxicity, effectiveness etc.) of the parent compound, such as are conventionally used in the pharmaceutical art.

The active compounds may be administered parenterally, e.g. by subcutaneous, intramuscular, or intravenous injection. Solutions or suspensions of these active compounds as a pharmaceutically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms. The peptide hormones of the present invention have a natural tendency to adhere to glass; therefore these preparations preferably also contain a pharmaceutically acceptable protein such as gelatin or albumin to competitively inhibit this effect.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, polyol (e.g., glycerol, propylene glycol and liquid polyethylene glycol), and suitable mixtures thereof. Compositions suitable for intramuscular or subcutaneous injection may also contain minor amounts of salts, acids, and bases to adjust tonicity and buffer the pH. Suitable pharmaceutically acceptable buffering and tonicity agents are readily determinable by persons skilled in the art.

Some of the compounds of this invention may also be suitable for oral administration, for example with an inert diluent or with an assimilable edible carrier, or they may be enclosed in hard- or soft-shell gelatin capsules, or they may be compressed into tablets, or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules, and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent may be added such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound, sucrose as a sweetening agent, methyl- and/or propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

A further understanding of this invention may be had from the following non-limiting examples. As used hereinabove and below unless expressly stated to the contrary, all temperatures and temperature ranges refer to the centigrade system and the terms ambient or room temperature refer to about 20° C. The term percent or (%) refers to weight percent and the terms mole and moles refer to gram moles.

EXAMPLE 1

Synthesis of MCT-I

MCT-I was synthesized by the solid phase method using a benzhydrylamine-substituted polystyrene resin crosslinked with 1% divinylbenzene. The C-terminal amino acid BocPro was coupled to the resin using HOBt and DCC. Thereafter, symmetric anhydrides of BocArg(N$^g$-Tos), BocCys(S-4-MeOBzl), BocGly, BocLeu, BocLys(N$^\epsilon$-2-ClZ), BocPro, BocSer(OBzl), BocThr(OBzl), and BocTrp(N$^{in}$-For) and a deprotection and coupling program similar to that employed by Yamashiro and Li, supra, was used, except for BocAsn, which was coupled by the HOBt/DCC method. Cleavage from the resin and removal of all the remaining protecting groups, except for the N$^{in}$-formyl, were accomplished by treatment with anhydrous liquid hydrofluoric acid in the presence of anisole (7:1, v/v) at 0° C. for 45 min. Crude peptide was removed from the resin by washing with 10% acetic acid. The residue remaining after lyophilization was treated with excess dithiothreitol in 0.05M sodium phosphate buffer at pH 7.0. The intramolecular disulfide bond between cysteine residues 1 to 7 was formed by diluting the peptide solution to a volume of 5 liters in the same buffer and adding a solution of 0.02M $K_3Fe(CN)_6$ slowly with stirring. The resultant dilute peptide solution was concentrated by passing it through a CM-Sephadex C-25 column, followed by a linear gradient of NaCl from 0.0 to 0.3M employing the same buffer. Fractions from this column were purified further by loading them directly onto a Waters $C_{18}$ TM semi-preparative HPLC column (Waters Associates, Milford, MA) and then eluting with a linear gradient of $CH_3CN$ from 20% to 50% in 0.2M sodium phosphate buffer, pH 2.5. After desalting the resultant solution, the N$^{in}$-formyl protecting group was removed quantitatively by treatment with 0.5M aqueous piperidine at 0° C. for 20 minutes. The deprotection reaction was terminated by the addition of acetic acid. Final purification was carried out by loading the reaction mixture directly onto the Waters $C_{18}$ semi-preparative column and eluting with 35% $CH_3CN$ in the same buffer. The yield of purified MCT-I after a final desalting step and lyophilization was 10% based on the original substitution level of BocPro. The peptide was judged to be pure based on the observation at 230 nm of a single peak when the peptide was eluted from a Waters $C_{18}$ reversed phase column using a gradient from 20% to 50% $CH_3CN$ as the eluting solvent and from its amino acid analysis after hydrolysis with 5.5M HCl.

Amino Acid Analysis: Arg 1.11 (1), Asp 2.01 (2), Cys 2.09 (2), Glu 5.00 (5), Gly 3.02 (3), Leu 7.14 (7), Lys 2.94 (3), Pro 1.63 (2), Ser 1.61 (2), Thr 3.5 (4).

EXAMPLE 2

Synthesis of MCT-II

MCT-II was synthesized by the solid phase method using a benzhydrylamine-substituted polystyrene resin crosslinked with 1% divinylbenzene by the method of Hruby, supra, in a Beckman 990 TM peptide synthesizer (Beckman Instruments). The C-terminal amino acid BocPro was coupled to the resin using HOBt and DCC. Thereafter, symmetric anhydrides of BocArg(N$^g$-Tos), BocCys(S-4-MeOBzl), BocGln, BocGly, BocLeu, BocLys(N$^\epsilon$2-ClZ), BocPro, BocSer(OBzl), BocThr(OBzl), and BocTyr(O-2,6-Cl$_2$Bzl) were used. An exception was BocAsn, which was coupled by the HOBt/DCC method. The deprotection and coupling program used was similar to that employed by Yamashiro and Li, supra. Cleavage from the resin and removal of all the remaining protecting groups was accomplished by treatment with anhydrous liquid hydrofluoric acid in the presence of anisole (7:1, v/v) at 0° C. for 45 min. Crude peptide was removed from the resin by washing with 10% aqueous acetic acid. A 200 mg portion of the residue remaining after lyophilization was treated with excess dithiothreitol in 5 ml of 0.05M sodium phosphate buffer at pH 7.5. The intramolecular disulfide bond between cysteine residues 1 and 7 was formed by diluting the peptide solution to a volume of 4 L in the same buffer and adding a solution of 0.02M $K_3Fe(CN)_6$ slowly with stirring until a persistent yellow color was obtained. The resultant dilute peptide solution was concentrated by passing it through a CM-Sephadex C-25 column, then eluted with a linear gradient of NaCl from 0.0M to 0.3M employing the same phosphate buffer. Fractions from this column were desalted on a Sephadex G-15 TM (Pharmacia Fine Chemicals) column and purified further by loading them onto a Zorbax $C_{18}$ TM (E. I. DuPont De Nemours & Co., Wilmington, DE) semi-preparative HPLC column equilibrated with 0.2M sodium phosphate buffer, pH 2.5, containing 20% $CH_3CN$. Peptide was eluted from the column with a linear gradient from 20% to 50% $CH_3CN$ in the same buffer. Fractions from HPLC were desalted using the G-15 column and lyophilized. The peptide was judged to be pure based on the observation of a single symmetrical peak when monitored at 230 nm as the peptide was eluted from an Altex Ultrasphere ODS TM (Rainin Instruments, Woburn, MA) analytical column using the same gradient and buffer as above and by its amino acid analysis after hydrolysis with HCl:trifluoroacetic acid (2:1 v/v).

Amino Acid Analysis: Arg 1.04 (1), Asx 1.67 (2), Glx 5.20 (5), Gly 1.75 (2), Leu 7.00 (7), Lys 3.15 (3), Ser 2.18 (3), Thr 2.94 (4), Tyr 0.98 (1).

EXAMPLE 3

Synthesis of MCT-III

The N-terminal 1-7 fragment of MCT-III was synthesized on a p-nitrobenzylphenone oxime resin by the method of Nakagawa, S. N. and E. T. Kaiser, J. Org. Chem. 48:678(1983). N$^\alpha$-Boc-aminooctanedioic acid-O$^\eta$-t-butyl ester was coupled to the resin using HOBt and DCC. N$^\alpha$-BocSer(OBzl)Thr(OBzl), N$^\alpha$-BocLeu, N$^\alpha$-BocAsn, and N$^\alpha$-BocSer were then sequentially coupled by the DCC/HOBt method. After deprotection of the N-terminal serine, the cyclic peptide was formed by stirring three equivalents of DCC and HOBt with the resin for 1 hr followed by the addition of three equivalents of diisopropylmethylamine. The cyclic peptide was cleaved from the oxime resin by shaking it with three equivalents of the acetate salt of leucine-t-butyl ester and three equivalents of acetic acid. The residue remaining after evaporating the solvent under vacuum was taken up in ethyl acetate. The cyclic peptide precipated and was collected by filtration. The t-butyl protecting group was removed by treatment with a mixture of trifluoroactic acid:anisole (3:1 v/v).

The C-terminal fragment of MCT-III was synthesized by the solid-phase method using a benzhydrylamine-substituted polystyrene resin crosslinked with 1% divinylbenzene as described by Hruby, supra, in a Beckman 990 peptide synthesizer. The C-terminal amino acid BocPro was coupled to the resin usng HOBt and DCC. Thereafter, symmetric anhydrides of BocArg(N$^\alpha$-Tos), BocCys(S-4-MeBzl), BocGln, BocGly, BocLeu, BocLys(N$^\epsilon$-2-ClZ), BocPro, BocThr(OBzl), and BocTyr(O-2,6-Cl$_2$Bzl) were used. The deprotection and coupling program used was similar to that employed by Yamashiro and Li, supra.

The N-terminal 1-7 fragment was finally coupled to the C-terminal fragment on the benzhydrylamine resin using DCC/HOBt and 50% dimethylformamide/methylene chloride. Cleavage from the resin and removal of all the remaining protecting groups was accomplished by treatment with anhydrous liquid hydrofluoric acid in the presence of anisole (7:1 v/v) at 0° C. for 45 min.

The crude peptide is removed from the resin and purified as in Example 2. The intramolecular disulfide bond between cysteine residues 19 and 24 in this example is formed according to the procedure given for cysteine residues 1 and 7 in Example 2.

EXAMPLE 4

Characterization of MCT-I

The circular dichroism (CD) spectra of MCT-I and salmon calcitonin (designated "SCT-I", available from Armour Pharmaceuticals, Kankakee, IL and used without further purification) from 250 nm to 205 nm show minima at 222 nm and 208 nm characteristic of α-helical structure. For MCT-I, the mean residue molar ellipticity at 222 nm, $[\theta]_{222}$, was $-7,800$ deg.cm$^2$/dmol ($10^{-4}$M peptide, 0.02M sodium phosphate buffer, 0.16M KCl, pH 7.4), from which the α-helicity was estimated to be 30% (assuming no contribution to CD by β-sheet structure) according to the method of Morisett, J. D., J. S. K. Davis, H. J. Pownall, and A. M. Gotto, Biochemistry 12:1290 (1973). The value of $[\theta]_{222}$ does not change over a range of concentration of MCT-1 from $10^{-7}$M to $10^{-4}$M, provided that binding to glass is prevented by pretreatment of the spectrometer cell with polyethylene glycol (MW 15K–20K). This suggests strongly that MCT-I remains monomeric over the concentration range employed, a conclusion supported by the measurement of a molecular weight of about 4,500 at a concentration of $10^{-4}$M MCT-I by means of ultracentrifugation using a Beckman Spinco Airfuge TM (Beckman Instruments, Berkeley, CA) according to the procedure of Pollet, R. J., B. A. Haase, and M. L. Standaert, J. Biol. Chem. 254:30 (1979). Similarly, the value of $[\theta]_{222}$ for solutions of SCT-I over the same concentration range and under the same conditions also remains constant at $-4,600$ deg.cm$^2$/dmol, leading to an estimate of 20% α-helix for this peptide. In 50% trifluoroethanol, a structure promoting solvent, both MCT-I and SCT-I were estimated to be 50% α-helical at a concentration of $5 \times 10^{-5}$M, as was found by Brewer, H. D. and H. Edelhoch, J. Biol. Chem. 245:2402 (1970) for porcine calcitonin (PCT) in 50% 2-chloroethanol.

For surface monolayer studies, a subphase of 0.01M Tris.HCl, pH 7.4 with 0.1M NaCl was prepared with glass-distilled water. Surfactant contaminants were removed by bubbling air through the solution for 10 min, then aspirating the surface of the buffer. Insoluble monolayers were spread from a $2.8 \times 10^{-4}$M solution of MCT-I in 0.1 mM HCl. The surface pressure $\pi$(dyn/cm) of the MCT-I monomolecular layer was measured as a function of area, A (cm$^2$), using a Lauda TM film balance (Brinkman Instruments, Norwalk, CT). At the air-water interface, MCT-I and SCT-I form insoluble monolayers when spread from concentrated solutions in 0.01M HCl. The force-area ($\pi$-A) curves between 5 and 12 dyn/cm are described by the equation $\pi[A - A_\infty(1 - \kappa\pi)] = nRT$ where $\kappa$ is a constant reflecting the compressibility of the monolayer and $A_\infty$ is the limiting molecular area extrapolated to zero surface pressure. The parameters calculated for the two peptides were very similar, $\kappa = 0.016$ cm/dyn for MCT-I and 0.02 cm/dyn for SCT-I, while $A_\infty = 362$ Å$^2$ for MCT-I and $A_\infty = 322$ Å$^2$ for SCT I. However, the collapse pressure of 24 dyn/cm found for the monolayer of MCT-I was much higher than the value of 14 dyn/cm observed for SCT-I.

EXAMPLE 5

In vitro Activity of MCT-I

Figure 2:
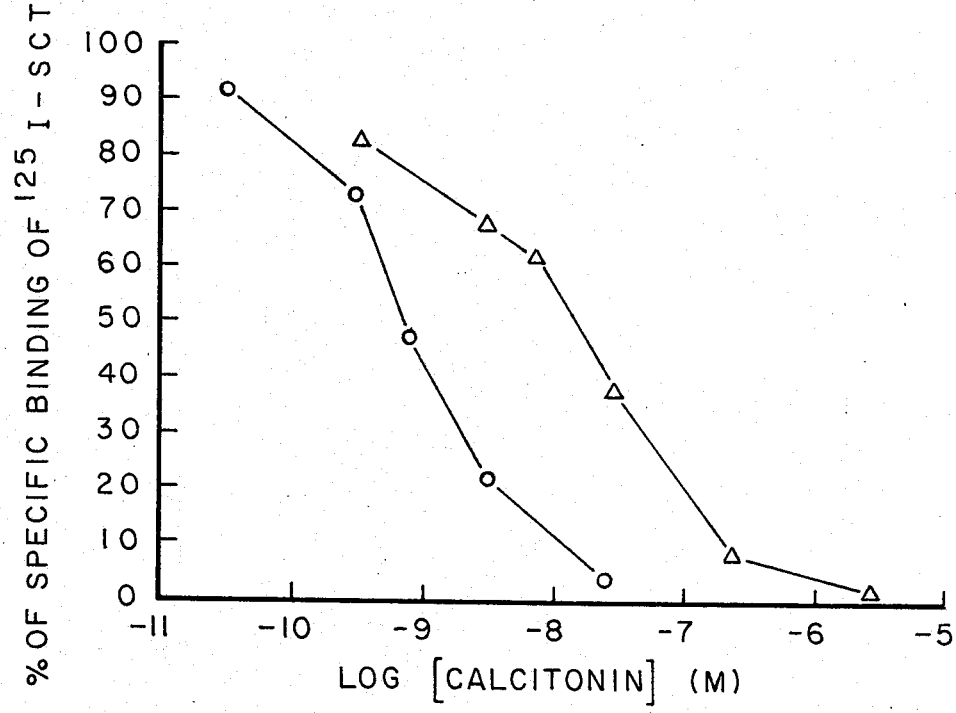

In order to study the receptor binding properties of MCT-I and SCT-I, [$^{125}$I] SCT-I was prepared by the method of Hunter, W. M. and F. C. Greenwood, Nature 194:495(1962). The iodinated hormone was purified by ion exchange chromatography on SP-Sephadex C-25 TM (Pharmacia Fine Chemicals). The unreacted labelling material was first washed from the column with 0.01M Tris-HCl, 0.1% bovine serum albumin (BSA), pH 7.4 buffer, followed by elution of the monoiodinated SCT-I with 0.2M NaCl at pH 8 in the same buffer. Fractions from the single symmetrical peak which was eluted with this buffer were combined, adjusted to pH 7.5, and frozen in small aliquots until needed. The specific activity of the radioiodinated peptide was $\sim 160$ $\mu$Ci/$\mu$g. Competitive binding experiments with rat brain homogenates were carried out as described by Nakamuta H., S. Furukawa, M. Koida, H. Yajima, R. C. Orlowski, and R. Schlueter, Japan J. Pharmacol. 31:53 (1981). This method has been shown to give binding curves for calcitonin analogues comparable to the more commonly used kidney binding assay, see Marx, S. J., C. J. Woodward, and G. D. Auerbach, Science 178:999 (1972), and the brain tissue is more convenient to prepare and use. The results are shown in FIG. 2, competitive inhibition of [$^{125}$I]-SCT-I binding to brain particulate fraction by SCT-I (O) and MCT-I (Δ). Each point represents the mean of three triplicate determinations. The binding curves obtained gave IC$_{50}$ values for SCT-I of about 2.5 nM, in agreement with the value reported earlier by Nakamuta et al., supra, and 17 nM for MCT-I which compares with the value of 17 nM found for porcine calcitonin (PCT) (Ibid.)

EXAMPLE 6

In vivo Activity of MCT-I

To assess the biological potency of MCT-I in vivo, male Sprague-Dawley rats (Charles River Breeding Laboratories, Wilmington, MA), 3–4 weeks old, were given subcutaneous injections (0.15 ml/100 g body weight) of SCT-I or MCT-I in 0.9% saline, 0.1% BSA, pH 4.5 in graded doses or, alternatively, of saline solution alone. Blood was withdrawn 1 hour after the injections, and the calcium concentration in the plasma determined by atomic absorption spectroscopy. The dose-response curve in FIG. 1 summarizes the results for SCT-I (O) and MCT-I (Δ). Each point represents the difference between the average serum Ca$^{+2}$ concentration for rats given only saline (20 rats per point) and the average for those given a particular dose of either MCT-I (15 rats per point) or SCT-I (5 rats per point). As with the binding studies, MCT-I is about 10-fold less potent than SCT-I, or approximately as active as PCT.

EXAMPLE 7

Characterization of MCT-II

Figure 3:
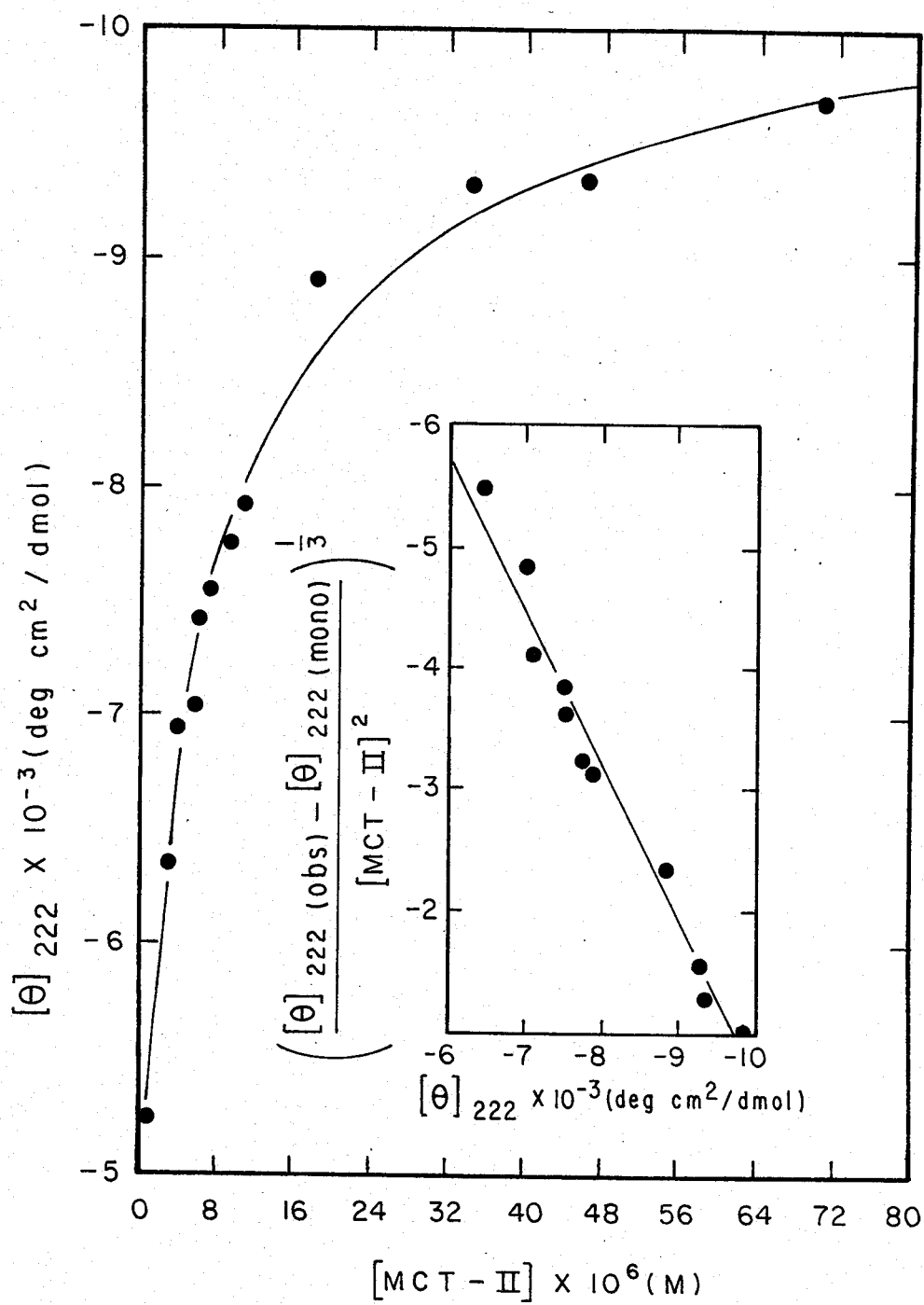

The circular dichroic spectra of MCT-II solutions buffered with 0.02M sodium phosphate at pH 7.4 and containing 0.16M KCl were measured from 250 nm to 200 nm using a Carey 60 TM spectropolarimeter (Varian Instruments, Palo Alto. CA). The spectrometer cells used were washed with concentrated nitric acid, rinsed thoroughly with deionized water, then treated with a 1% aqueous polyethylene glycol (M$_r$ 15K–20K)

solution for 1 hr and finally rinsed with water before using. The molar ellipticities obtained from the circular dichroic spectra of MCT-II from 240 nm to 204 nm were fitted by a linear combination of three different basis functions derived from the spectra described by Greenfield, N. and G. D. Fasman, Biochem. 8:4108(1969) for α-helix, β-sheet, and random coil structure. This analysis indicated that MCT-II exists in solution as a mixture of α-helical and random coil structure. Since there was no significant contribution to the spectrum from β-sheet structure, we used the mean residue molar ellipticity at 222 nm, $[\theta]_{222}$, to estimate changes in α-helical structure (Morrisett et al., supra). The results are given in FIG. 3; each data point represents the mean from two experiments. $[\theta]_{222}$ exhibited a concentration-dependent decrease above $4.2 \times 10^{-7}$M MCT-II that was consistent with monomer/trimer equilibrium. $[\theta]_{222}$ for the monomer was $-5,200$ deg.cm$^2$/dmol (20% α-helix) and $-10,475$ deg.cm$^2$/dmol (35% α-helix) for the trimer. A plot of $[\theta]_{222}$ versus $(([\theta]_{222}-[\theta]_{222} \text{ monomer})/[\text{MCT-II}]^2)^{\frac{1}{3}}$ (inset in FIG. 3) yielded a dissociation constant ($K_d$) for the oligomer of $5.06 \times 10^{-11}$M$^2$. This dissociation constant corresponds to a 4.5 kcal/mol of stabilization energy per monomer for trimerization. Under similar conditions and over the same concentration range $[\theta]_{222}$ for MCT-I and SCT-I remained constant at $-7,800$ deg.cm$^2$/dmol and $-4,600$ deg.cm$^2$/dmol, respectively.

The molecular weights of MCT-I, MCT-II, and SCT-I ($1 \times 10^{-3}$M peptide in 0.02M sodium phosphate buffer, pH 7.4, containing 0.16M KCl and 7 mg/ml Dextran T-40 TM (Pharmacia Fine Chemicals)) were determined by sedimentation equilibria using a Beckman Spinco Airfuge according to the procedure of Pollet et al., supra. The peptide concentration in each successive 10 μl aliquot removed from the centrifuge tube was determined by derivitizing with fluorescamine and measuring the fluoresecence intensity ($\lambda_{ex}$ 390 nm, $\lambda_{em}$ 480 nm) using a Perkin-Elmer 650-40 TM fluorescence spectrometer (Perkin-Elmer Instruments, Wilton, CT). The molecular weight of MCT-II determined by sedimentation equilibrium was $10,045 \pm 645$ g/mol or 2.8 times the monomer molecular weight of 3563 g/mol and is consistent with CD evidence for a monomer/trimer equilibrium. MCT-I also appeared to be trimeric at $1 \times 10^{-3}$M concentration with molecular weight ($M_r$) = $10,658 \pm 213$ ($3.0 \times$ monomer) despite self-association in CD experiments not being detected up to $1 \times 10^{-4}$M. This suggests MCT-I may be aggregating only at relatively very high concentrations. SCT-I appears to be monomeric at $1 \times 10^{-}$M with $M_r$ calculated to be $3456 \pm 60$ g/mol compared with the theoretical monomer molecular weight of 3435 g/mol.

Surface monolayer studies were conducted as in Example 4. MCT-II forms stable monolayers at the air-water interface when spread from concentrated solutions in 0.01M HCl. The force-area curve ($\pi - A$) between 0 dyn/cm and 21 dyn/cm can be described by the equation $\pi(A - A_\infty(1-\kappa\pi)) = nRT$ where $A_\infty$ is the limiting molecular area extrapolated to zero surface pressure and $\kappa$ is a constant reflecting the compressibility of the monolayer. The parameters calculated using the entire $\pi - A$ curve indicate that MCT-II forms a compact, relatively rigid structure at the air-water interface. $A_\infty$ was $362 \pm 10$ Å$^2$ compared with $434 \pm 7$ Å$^2$ for MCT-I and $559 \pm 18$ Å$^2$ for SCT-I. Monolayers of SCT-I, MCT-I, and MCT-II were successively less compressible with $\kappa$ having values of 0.03 cm/dyn for SCT-I, 0.02 cm/dyn for MCT-I, and 0.01 cm/dyn for MCT-II. Collapse of the monolayer occurred at 22 dyn/cm which was slightly lower than the 24 dyn/cm observed for MCT-I and higher than for the SCT-I monolayer which collapses at 12 dyn/cm.

EXAMPLE 8

Binding of MCT-I and MCT-II to Single Bilayer Egg Lecithin Vesicles

Egg lecithin single bilayer vesicles (SBVs) were prepared by rapid injection of an ethanolic egg yolk lecithin (Avanti Polar-Lipids Inc., Birmingham, AL) solution into aqueous 0.16M KCl by the method of Batzri, S. and E. D. Korn, Biochim. Biophys. Acta 298:1015(1973) and purified by filtration through a 2.5 cm × 87 cm column of Fractogel TSK HW-75(F) TM (Pierce Chemical Co., Rockford, IL). After purification, vesicles were characterized by gel filtration through a 1.5 cm × 40 cm column of Sepharose CL-4B TM (Pharmacia Fine Chemicals) by the method of Batzri and Korn, supra. The concentration of vesicles in stock solutions were determined by the phosphate assay of Ames, B. N. and D. T. Dubin, J. Biol. Chem. 235:769(1960). In a typical binding experiment, varying concentrations of peptide were incubated for 45 min at 21° C. with vesicles ($7 \times 10^{-4}$M lecithin) in 0.02M sodium phosphate buffer, pH 7.4 containing 0.16M KCl in a total volume of 300 μl for 45 min. Free peptide was separated from vesicle-bound peptide by rapid filtration through a 1.4 cm × 6.3 cm column of Sepharose CL-6B TM (Pharmacia Fine Chemicals) using the same buffer as above the eluent. The concentration of peptide in each fraction was determined using fluorescamine after first disrupting the vesicles with isopropanol (20% by volume).

Figure 4:
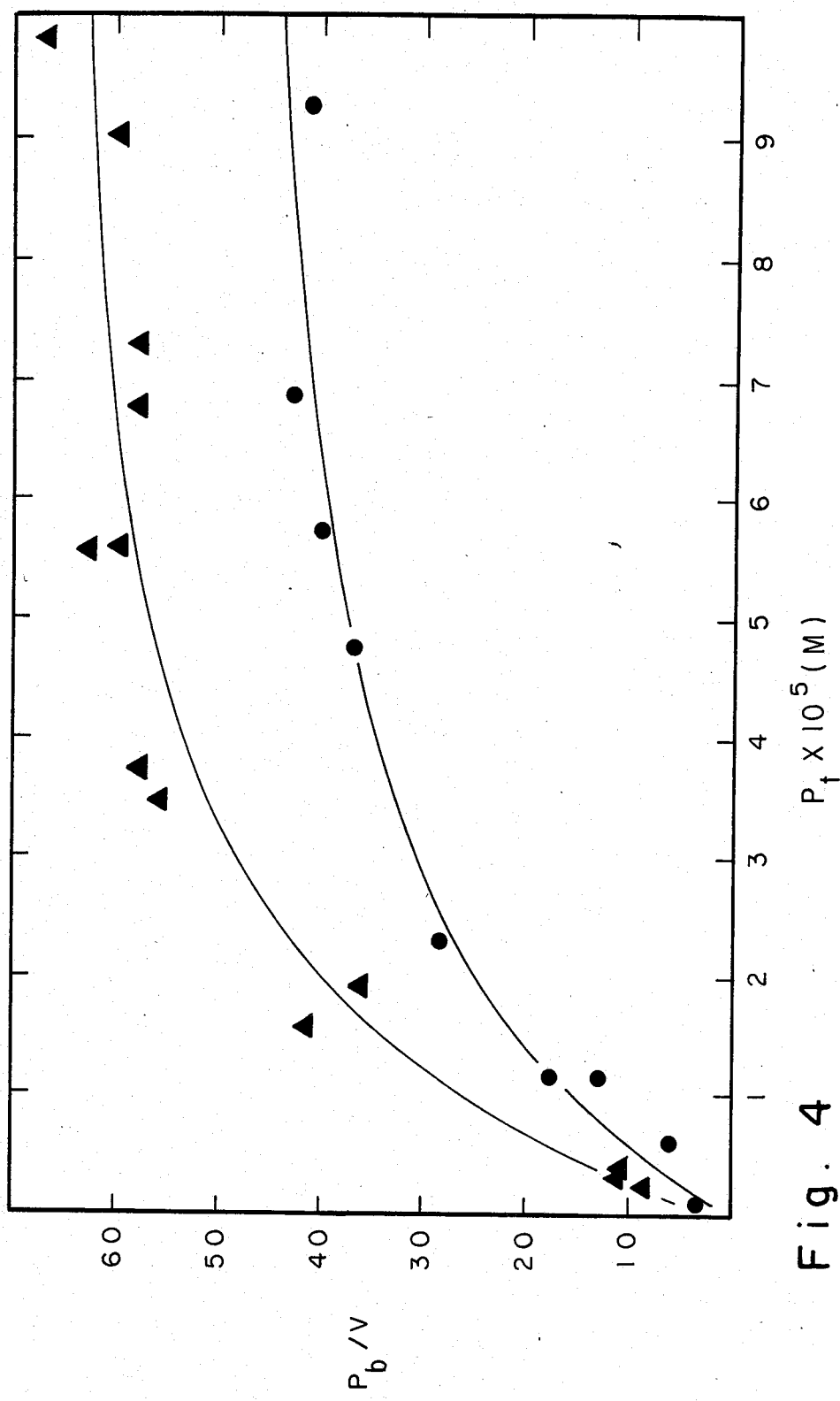

As shown in FIG. 4 (SCT-I=(O), MCT-I=(Δ)), both MCT-I and MCT-II adsorb to the surface of single bilayer egg lecithin vesicles at concentrations between 1 and 100 μM peptide. There was no detectable adsorption of SCT-I to vesicles at similar concentrations of peptide and vesicles at either pH 7.4 or pH 3.0. The data for MCT-I and MCT-II were analyzed according to the equation $P_f = (N \cdot V \cdot P_f / P_b) - K$ (Adamson, A. W., Physical Chemistry of Surfaces, 3rd Ed. (Wiley Interscience, New York, 1976), p. 388), where $P_f$ and $P_b$ are the concentration of free and bound peptide respectively, V is the initial molarity of vesicles (3200 phospholipids per vesicle), N is the upper limit of $P_f/V$, and K is the dissociation constant. Plots of $V \cdot P_f/P_b$ versus $P_f$ were linear and gave $K = 12.9 \pm 4.8$ μM with $N = 50 \pm 5$ for MCT-I and $K = 6.7 \pm 1.7$ μM, $N = 68 \pm 2$ for MCT-II. The product, $A_\infty \cdot N$, where $A_\infty$ was obtained from the monolayer studies in Example 7, are nearly the same ($A_\infty \cdot N_{(MCT-I)} = 2.2 \pm 0.2 \times 10^4$ Å$^2$, $A_\infty \cdot N_{(MCT-II)} = 2.5 \pm 0.1 \times 10^4$ Å$^2$), accounting for the difference in observed values of N. $A_\infty \cdot N$ is also in reasonable agreement with estimates of the available surface area between the phospholipid head groups of 230 Å diameter vesicles ($1.8 \pm 0.6 \times 10^4$ Å$^2$; Kupferberg, J. P., S. Yokoyama, and F. J. Kezdy, J. Biol. Chem. 256:6274(1981)). Analytical Sepharose CL-4B gel filtration of vesicles after incubation with MCT-I or MCT-II at concentrations above $1 \times 10^{-4}$M showed that their structure was disrupted, resulting in the formation of a smaller molecular weight species, possibly peptide/lipid micelles.

EXAMPLE 9

In vitro Activity of MCT-II

[$^{125}$I]SCT-I (specific activity 150 µCi/µg) was prepared by the method of Hunter and Greenwood, supra, using Na[$^{125}$I] purchased from New England Nuclear Corp., Boston, MA. Iodinated hormone was purified by ion-exchange chromatography on SP-Sephadex C-25 and stored until needed in 50 µl aliquots of ~3000 CPM/µl at −20° C.

Crude rats brain membranes were prepared as described by Nakamuta et al., supra, using 250-300 gm male Sprague-Dawley rats (Charles River Breeding Laboratories). Membranes were either used immediately or stored at −80° C. for no more than three days. Crude rat kidney membranes used for binding studies and adenylate cyclase assays were prepared as described by Schwartz, K. E., R. C. Orlowski and R. Marcus, Endocrinology 108:831 (1981) with a minor modification. The dissected kidney cortices were first homogenized briefly with a Polytron ™ (Brinkman Instruments) at low speed ("5") before complete homogenization with a loose-fitting Wheaton Dounce homogenizer (American Scientific Products, MacGaw Park, IL, pestle "B"). Protein concentrations were determined using Coomassie Brilliant Blue G-250 (Sedmak, J. J. and S. E. Grossberg, Anal. Biochem. 83:544 (1977)) and crystallized BSA (Sigma Chemical Co., St. Louis, MO) as the standard. All preparations of kidney membranes were carried out at 4° C. and the membranes were used immediately for binding studies or adenylate cyclase assays.

In both brain and kidney binding studies, a set of 1.5 ml polyethylene tubes were first pretreated with a specific concentration of MCT-II or SCT-I, [$^{125}$I]SCT-I tracer, and buffer (50 mM Tris.HCl, pH 7.4 containing 35 µM bacitracin). The mixture was aspirated after a 1 hr incubation and these tubes were reused for all experiments, one set for brain membrane binding experiments and one set for kidney membrane binding experiments. In the actual binding assays, each pretreated tube contained membrane suspension (0.5-1 mg protein), 15,000-20,000 CPM [$^{125}$I]SCT-I, and from 0-1 µM cold peptide in the same Tris buffer described above in a final volume of 1 ml. Incubations were continued for 30 min at 4° C. (brain membranes) or 40 min at 21° C. (kidney membranes), and then stopped by centrifuging the tubes at 13,000 rpm for 5 min on a Beckman Microfuge II ™ (Beckman Instruments). The supernatant was aspirated and the pellet collected by aspiration into a 200 µl disposable pipet tip packed with glass wool. Radioactivity in each tip was quantitated using a Beckman Gamma 5500 ™ counter (Beckman Instruments).

Figure 5:
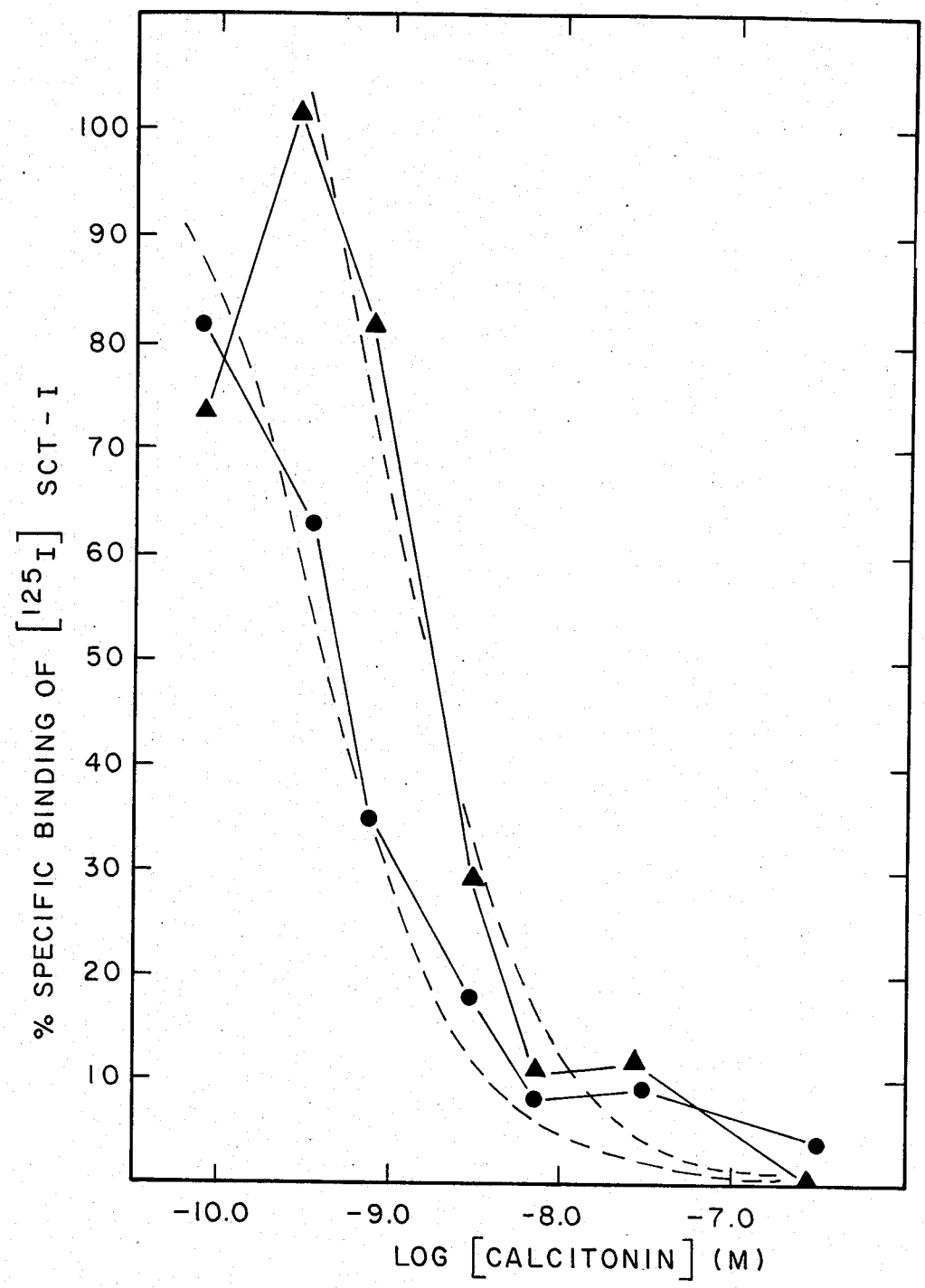
Figure 6:
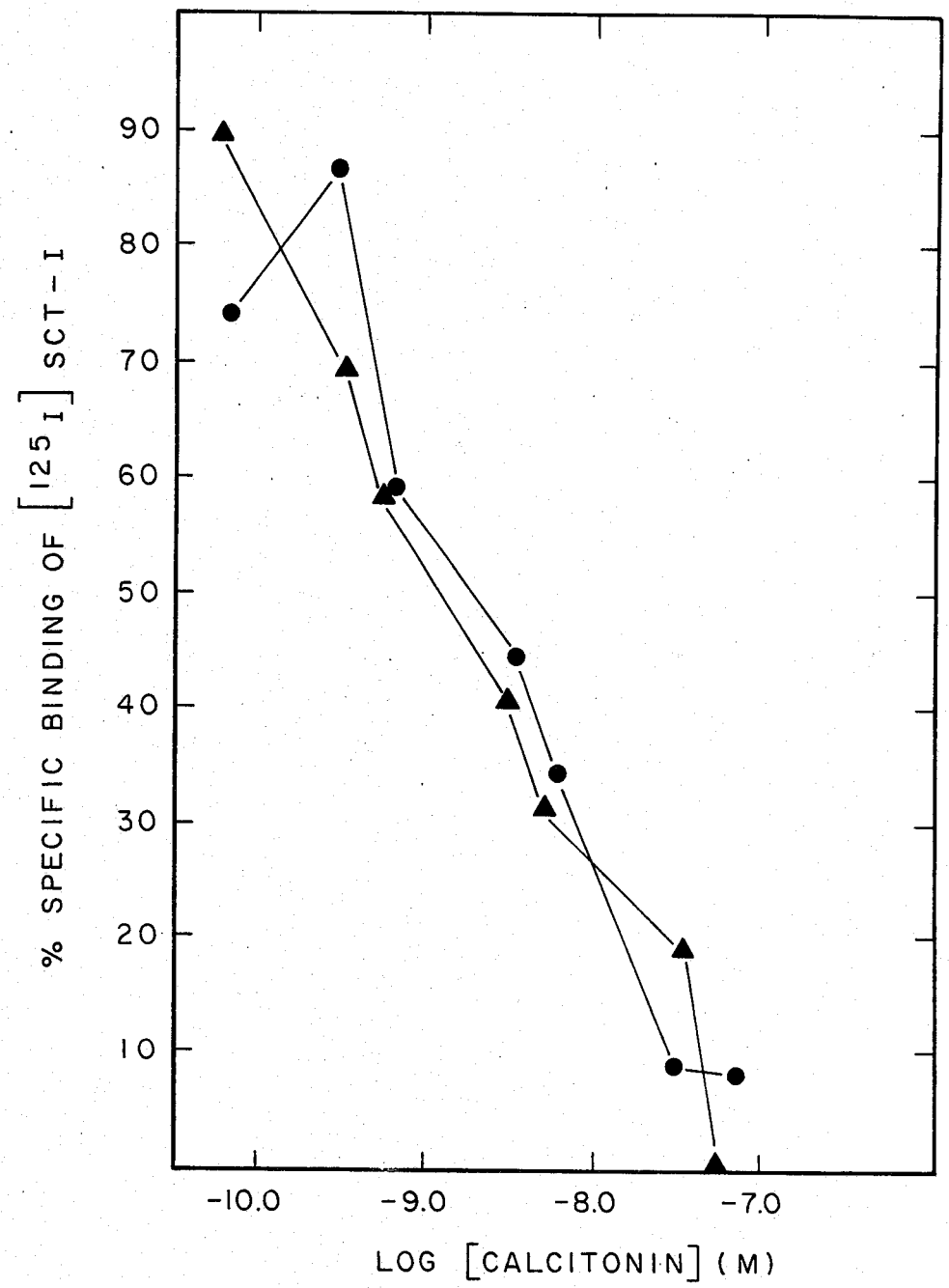

Preliminary binding experiments with both brain and kidney membranes were hampered by nonspecific binding of MCT-II to the plastic incubation tubes. This non-specific binding was not inhibited by 35 µM bacitracin or BSA at concentrations as high as 2%. However, using tubes pretreated with peptide as described above allowed us to obtain displacement curves of [$^{125}$I]SCT-I by MCT-II comparable to those of SCT-I (FIGS. 5 and 6; SCT-I=(O), MCTII=(Δ); each point represents the mean of three triplicate determinations). As shown in FIG. 5, the curve for MCT-II in the brain binding experiment had an unusual shape. A theoretical curve for competitive binding of single ligands to independent binding sites can be represented as % Specific Binding=

$$\frac{100}{C + P_o/CK_p}$$

where C is the ratio of the total concentration of receptor-bound [$^{125}$I]-SCT-I in the absence of competitive ligand to the concentration in the presence of competitive ligand, and $P_o$ and $K_p$ are, respectively, the initial concentration and dissociation constant of the competitive ligand (see dashed lines in FIG. 5); this curve could be fitted to the data points for concentrations of MCT-II above 0.3 nM. Thus, the anomaly probably is an artifact of strong, non-specific interactions between MCT-II and the membrane vesicles. For brain receptors, $IC_{50}$ values calculated from theoretical curves fitted to the data were 0.4 nM for SCT-I and 0.6 nM for MCT-II. With the crude kidney membranes SCT-I and MCT-II appeared to have identical potency and $IC_{50}$ values of approximately 1.5 nM. The $IC_{50}$ for SCT-I in the brain membrane binding experiments was slightly lower than that determined in control experiments carried out in tubes that had not been pretreated ($IC_{50}$=1 nM), but was unchanged in experiments employing kidney membranes under both conditions.

Figure 7:
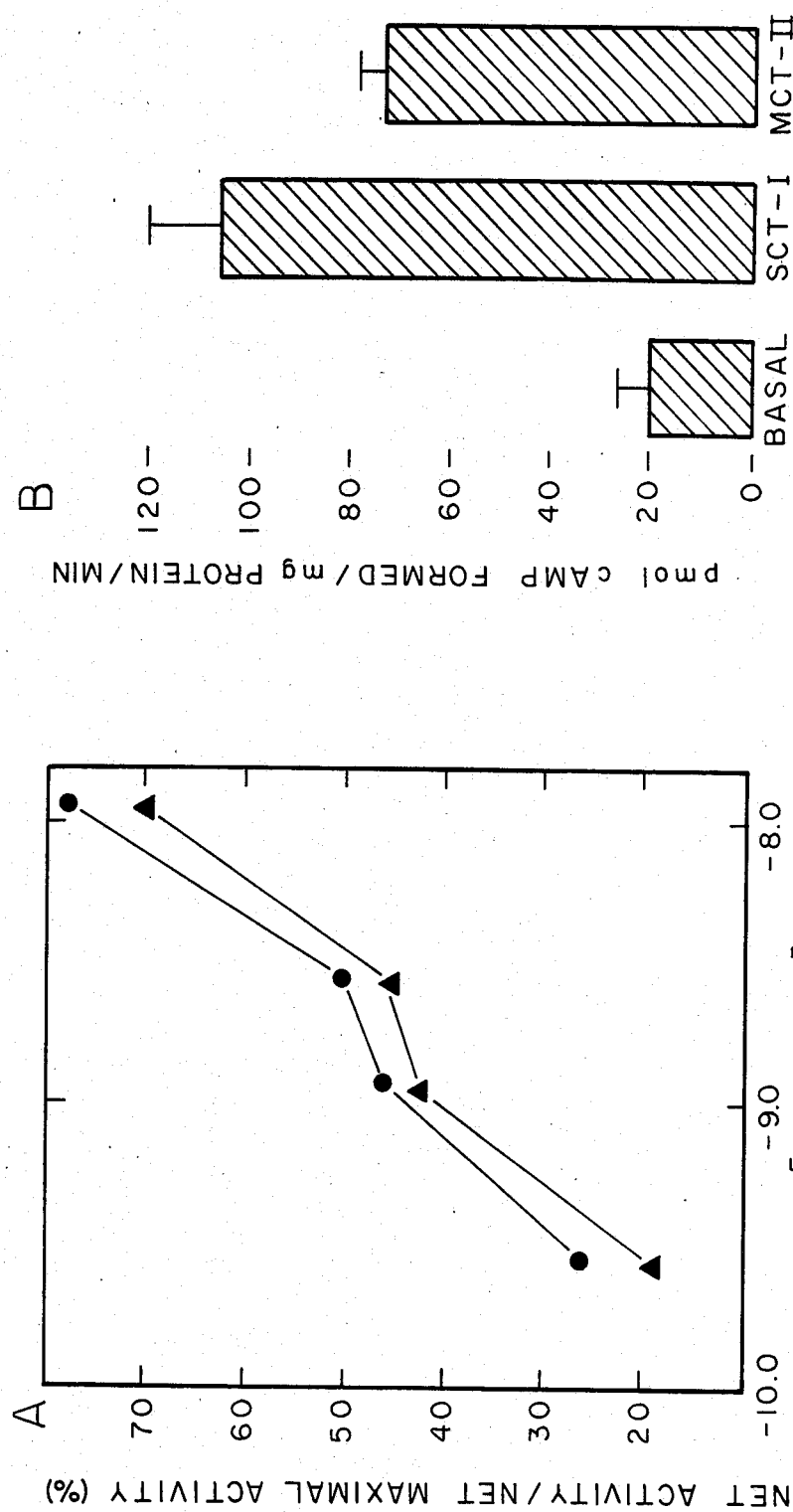

Peptide stimulation of adenylate cyclase activity in crude kidney cortical membranes was measured using methods described by Marcus, R. and G. D. Aurbach, Biochim. Biophys. Acta 242:410 (1971). The reaction mixture contained 1 mM [α-$^{32}$P]ATP (Amersham, Arlington Heights, IL) (specific activity 70-100 CPM/pmol), 1 mM [$^3$H]cAMP (Amersham) (approximately 40,000 CPM), 1 mM EDTA, 1 mM ethyleneglycol-bis-(β-aminoethylether)-N,N,N',N'-tetraacetic acid (EGTA), 5 mM MgCl$_2$, 25 mM Tris.HCl (pH 7.5), 10-20 µg membrane protein, hormone (except for control tubes) and an ATP-regenerating system consisting of 20 mM creatine phosphate, 0.2 mg/ml creatine kinase, and 20 µg/ml myokinase in a total volume of 100 µl. The reaction was initiated by the addition of membranes. Incubations were continued for 10 min at 37° C. and terminated by the addition of 100 µl of a solution containing 10 mM cAMP, 40 mM ATP, and 1% sodium dodecyl sulfate, followed by boiling for 3 min. cAMP was isolated using the method given by Birnbaumer, L., P. C. Yang, M. Hunzicker-Dunn, J. Bockaert, and J. W. Duran, Endocrinology 99:163 (1976). Both SCT-I and MCT-II stimulated adenylate cyclase over basal activity (FIG. 7: (A) Effect of increasing concentrations of SCT-I (O) and MCT-II (Δ) on rat kidney adenylate cyclase activities. Adenylate cyclase activity is expressed as the enzyme activity above basal stimulated by SCT-I or MCT-II (net activity) divided by the maximal stimulated enzyme activity above basal (net maximal activity)×100. Each point is the mean of duplicate determinations from two separate assays. (B) The mean maximal adenylate cyclase activity expressed as pmol cAMP formed/mg protein/min. Error bars indicate the S.E.). SCT-I produced a slightly higher maximal stimulation and was slightly more active over the same range of concentration. However, this difference is probably not large enough to be significant when the high non-specific binding of MCT-II encountered in membrane receptor assays and the identical potency observed for SCT-I and MCT-II in these assays and in the in vivo assay are considered.

EXAMPLE 10

In vivo Activity of MCT-II

The relative hypocalcemic potency of MCT-II and SCT-I was assessed by giving 3 to 4 week-old male Sprague-Dawley rats (Charles River Breeding Laboratories) subcutaneous injections of hormone in 0.9% saline containing 0.1% BSA. In each experiment, 25 rats were divided into 5 groups of 5 rats each and each group given either saline alone or saline with hormone. Blood samples were obtained by cardiac puncture from the ether-anesthetized rats 1 hr after injection. 200 µl of the blood plasma was diluted in 5 ml of 5% trichloroacetic acid-1000 ppm lithium (Chem-Chek Consulting Inc., South Boundbrook, NJ) and centrifuged before determining the calcium concentration by plasma emission spectrometry (Beckman Spectra Span IV TM, Beckman Instruments). Calcium standards were also purchased from Chem-Chek Consulting Inc.

Figure 8:
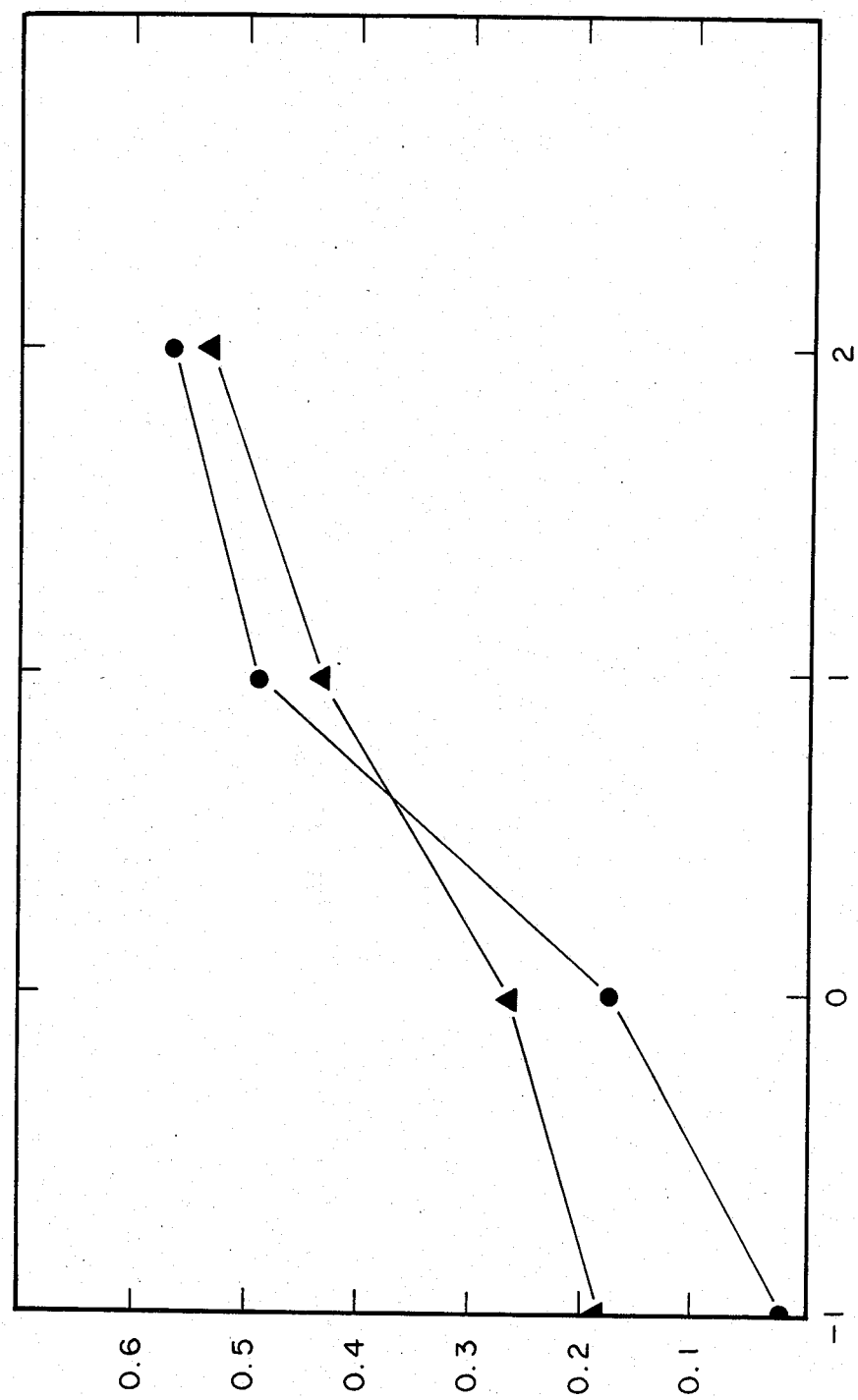

In two experiments using different groups of rats, the hypocalcemic potency of MCT-II was indistinguishable from that of our preparation of SCT-I over a dosage range of from 0.1 to 100 ng/100 g body weight (FIG. 8: log-dose response curves for SCI-I (O) and MCT-I (Δ). Each point represents the difference between the mean serum calcium concentrations [$Ca^{+2}$] for rats given only saline and the mean for those given a particular dose of either SCT-I or MCT-II in two separate experiments).

Although the sequence of amino acids in MCT-I differs from that in SCT-I at positions 2,8,10–15,17, and 20–22, the MCT-I reproduced all of the chemical and biological properties of the salmon calcitonin that were examined. Moreover, MCT-I displaced a specifically bound ligand from calcitonin receptors in vitro and effected a potent hypocalcemic response in the rat bioassay. Although MCT-I differs from PCT at 21 out of 32 sites (2, 8, 10–15, 17–27, 29–30) in its amino acid sequence, the in vitro and in vivo activity of MCT-I is equivalent to that of PCT, the most potent commercially available calcitonin.

MCT-II differs from SCT-I at 9 sites (positions 8, 10–11, 13–15, 17, and 20–21), and from MCT-I at 3 sites (positions 2, 12, and 22); yet in all assays used to compare them, MCT-II is as active as SCT-I and 10 times as active as MCT-I.

Taken together, these examples clearly demonstratee that it is not the linear (primary) sequence of the calcitonins which is a factor in biological activity, but rather the proper three-dimensional secondary structure of the peptide which is crucial. Prior to the present invention, all synthetic analogs of calcitonin involved simple substitutions in the primary sequences of the natural calcitonins, without understanding of, or consideration for, the importance of secondary structure. As a result, none of the analogs produced had activity equal to that of SCT, the most potent natural calcitonin.

By contrast, the present invention demonstrates that the amphiphilic α-helicity of the calcitonins is a major factor in activity, and that the region from residues 8–22 (Section 2) of the compounds of Formula I plays a crucial structural role in interacting in the α-helical form with the amphiphilic environment of the calcitonin receptor. In addition, these examples show that a hydrophilic residue in position 15 (as found in all natural calcitonins) is not required for high biological activity, but that receptor binding is sensitive to steric interactions on the hydrophobic face of the α-helix. Although the calcitonin receptor system apparently involves many complex interactions between ligand and receptor, we have shown that the compounds of the present invention, designed to possess amplified α-helical structure within the context of the appropriate structural conformation as shown in Formula I, are active and that in some cases this activity is superior to that of any previously known synthetic analog.

Further examples of compounds and applications within the spirit and scope of this invention will be apparent to those skilled in the art upon consideration of the foregoing description and consequently only such limitations as appear in the appended claims should be placed thereon.

We claim:

1. A compound of the formula:

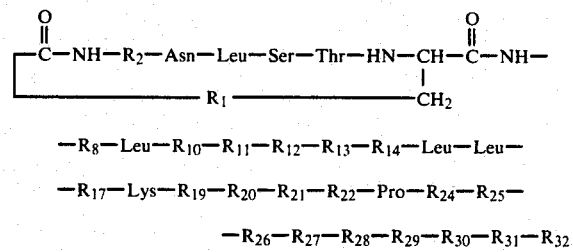

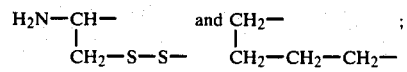

$-R_8-Leu-R_{10}-R_{11}-R_{12}-R_{13}-R_{14}-Leu-Leu-$ $-R_{17}-Lys-R_{19}-R_{20}-R_{21}-R_{22}-Pro-R_{24}-R_{25}-$ $-R_{26}-R_{27}-R_{28}-R_{29}-R_{30}-R_{31}-R_{32}$ wherein $R_1$ is a moiety selected from the group consisting of $$H_2N-CH- \quad \text{and} \quad CH_2- \\ | \qquad\qquad\qquad | \\ CH_2-S-S- \quad\quad CH_2-CH_2-CH_2-$$

$R_2-R_{22}$ are amino acid moieties wherein $R_2$ is absent, Ser or Gly, $R_8$ is Leu or Val, $R_{10}$ is Gln, Lys, or Gly, $R_{11}$, $R_{14}$, and $R_{20}$ are each independently selected from the group consisting of Gln and Lys, $R_{12}$ is Leu or Trp, $R_{13}$ is Gln or Ser, $R_{17}$ is Gln or His, $R_{19}$ is Leu or Cys, $R_{21}$ is Gln or Thr, $R_{22}$ is absent Leu and Tyr;

$R_{24}$-$R_{31}$ comprise a series of eight amino acids each independently selected from the group consisting of Gly, Ser, Thr, Cys, Tyr, Asn, Gln, Asp, Glu, Lys, Arg, and His, with the proviso that not more than one of said eight amino acids may be selected from the group consisting of Asp, Glu, Lys, Arg, and His; and with the proviso that no four or more of said eight amino acids will spontaneously form helical, β-sheet, or β-turn configurations; with the further proviso that when $R_{19}$ is Cys, $R_{24}$ must also be Cys linked to $R_{19}$ via a disulfide bridge; and $R_{32}$ is an amino acid amide selected from the group consisting of proline amide and glycine amide;

and the pharmaceutically acceptable salts thereof.

2. The compound according to claim 1 wherein $R_8$ is Leu; $R_{10}$ is Gln or Lys; and $R_{13}$, $R_{17}$, and $R_{21}$ are each Gln.

3. The compound according to claim 1, wherein $R_1$ is $$\begin{array}{c} H_2N-CH- \\ | \\ CH_2-S-S- \end{array}$$

4. The compound according to claim 2, wherein $R_1$ is $$\begin{array}{c} H_2N-CH- \\ | \\ CH_2-S-S- \end{array}$$

5. The compound according to claim 1, wherein $R_1$ is $$\begin{array}{c} CH_2- \\ | \\ CH_2-CH_2-CH_2- \end{array}$$

6. The compound according to claim 2, wherein $R_1$ is $$\begin{array}{c} CH_2- \\ | \\ CH_2-CH_2-CH_2- \end{array}$$

7. The compound according to claim 4 of the formula:

H₂N—Cys—Ser—Asn—Leu—Ser—Thr—Cys—Leu—Leu—
          |_____|

—Gln—Gln—Leu—Gln—Lys—Leu—Leu—Gln—Lys—
—Leu—Lys—Gln—Tyr—Pro—Arg—Thr—Asn—Thr—

$$-Gly-Ser-Gly-Thr-Pro\overset{O}{\overset{\|}{C}}NH_2$$

and the pharmaceutically acceptable salts thereof.

8. The compound according to claim 6 of the formula:

$$\begin{array}{c} \phantom{CH_2-}\overset{O}{\overset{\|}{C}}\phantom{-NH-Ser-Asn-Leu-Ser-Thr-CH}\overset{O}{\overset{\|}{C}} \\ CH_2-C-NH-Ser-Asn-Leu-Ser-Thr-CH-C-NH- \\ | \phantom{CH_2-C-NH-Ser-Asn-Leu-Ser-Thr-CH-C-NH-} | \\ CH_2-\!\!-\!\!-\!\!-\!\!-CH_2-\!\!-\!\!-\!\!-\!\!-CH_2-\!\!-\!\!-\!\!-\!\!-CH_2 \end{array}$$

—Leu—Leu—Gln—Gln—Leu—Gln—Lys—Leu—Leu—

—Gln—Lys—Cys—Lys—Gln—Tyr—Pro—Cys—Thr—
              |_____|

$$-Gly-Thr-Gly-Thr-Gly-Thr-Pro\overset{O}{\overset{\|}{C}}NH_2$$

and the pharmaceutically acceptable salts thereof.

9. A method of lowering serum plasma calcium levels in warm-blooded animals comprising administering to said warm-blooded animal a serum plasma calcium-lowering effective amount of a compound according to claim 1.

10. A method of lowering serum plasma calcium levels in warm-blooded animals comprising administering to said warm-blooded animal a serum plasma calcium-lowering effective amount of a compound according to claim 2.

11. A method of lowering serum plasma calcium levels in warm-blooded animals comprising administering to said warm-blooded animal a serum plasma calcium-lowering effective amount of a compound according to claim 3.

12. A method of lowering serum plasma calcium levels in warm-blooded animals comprising administering to said wrm-blooded animal a serum plasma calcium-lowering effective amount of a compound according to claim 4.

13. A method of lowering serum plasma calcium levels in warm-blooded animals comprising administering to said warm-blooded animal a serum plasma calcium-lowering effective amount of a compound according to claim 5.

14. A method of lowering serum plasma calcium levels in warm-blooded animals comprising administering to said warm-blooded animal a serum plasma calcium-lowering effective amount of a compound according to claim 6.

15. A method of lowering serum plasma calcium levels in warm-blooded animals comprising administering to said warm-blooded animal a serum plasma calcium-lowering effective amount of a compound according to claim 7.

16. A method of lowering serum plasma calcium levels in warm-blooded animals comprising administering to said warm-blooded animal a serum plasma calcium-lowering effective amount of a compound according to claim 8.

17. A composition of matter suitable for use in lowering serum plasma calcium levels in warm-blooded mammals, said composition comprising a compound according to claim 1 in conjunction with a pharmaceutically acceptable carrier.

18. A composition of matter suitable for use in lowering serum plasma calcium levels in warm-blooded mammals, said composition comprising a compound according to claim 2 in conjunction with a pharmaceutically acceptable carrier.

19. A composition of matter suitable for use in lowering serum plasma calcium levels in warm-blooded mammals, said composition comprising a compound according to claim 3 in conjunction with a pharmaceutically acceptable carrier.

20. A composition of matter suitable for use in lowering serum plasma calcium levels in warm-blooded mammals, said composition comprising a compound according to claim 4 in conjunction with a pharmaceutically acceptable carrier.

21. A composition of matter suitable for use in lowering serum plasma calcium levels in warm-blooded mammals, said composition comprising a compound according to claim 5 in conjunction with a pharmaceutically acceptable carrier.

22. A composition of matter suitable for use in lowering serum plasma calcium levels in warm-blooded mammals, said composition comprising a compound according to claim 6 in conjunction with a pharmaceutically acceptable carrier.

23. A composition of matter suitable for use in lowering serum plasma calcium levels in warm-blooded mammals, said composition comprising a compound of the formula H₂N—Cys—Gly—Asn—Leu—Ser—Thr—Cys—Leu—Leu—
          |_____|

—Gln—Gln—Trp—Gln—Lys—Leu—Leu—Gln—Lys—
—Leu—Lys—Gln—Leu—Pro—Arg—Thr—Asn—Thr—

-continued

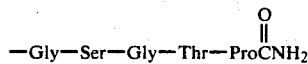

and the pharmaceutically acceptable salts thereof, in conjunction with a pharmaceutically acceptable carrier.

24. A composition of matter suitable for use in lowering serum plasma calcium levels in warm-blooded mammals, said composition comprising a compound according to claim 7 in conjunction with a pharmaceutically acceptable carrier.

25. A composition of matter suitable for use in lowering serum plasma calcium levels in warm-blooded mammals, said composition comprising a compound according to claim 8 in conjunction with a pharmaceutically acceptable carrier.

* * * * *

UNITED STATES PATENT AND TRADEMARK OFFICE
CERTIFICATE OF CORRECTION

PATENT NO. : 4,663,309
DATED : May 5, 1987
INVENTOR(S) : E.T. Kaiser and G.R. Moe It is certified that error appears in the above—identified patent and that said Letters Patent is hereby corrected as shown below:

Column 1, line 46: Delete "Physilogy" and insert

-- Physiology --.

Column 3, line 16: Delete "20:148 1 (1979)" and insert

-- 20:148 (1979) --.

Column 4, line 65: Delete "43:3552" and insert -- 42:3552 --.

Column 4, line 68: Delete "(Bα)" and insert -- (Boc) --.

Column 18, line 48: Insert a comma between "absent" and "Leu".

Signed and Sealed this

Twenty-fourth Day of May, 1988

Attest:

DONALD J. QUIGG

Attesting Officer

Commissioner of Patents and Trademarks